United States Patent [19]

Debras et al.

[11] Patent Number: 4,587,375

[45] Date of Patent: May 6, 1986

[54] PROCESS FOR THE ISOMERIZATION OF OLEFINS

[75] Inventors: Guy L. G. Debras, Belgrade; Georges E. M. J. De Clippeleir, Sint Pieters; Raymond M. Cahen, Brussels, all of Belgium

[73] Assignee: Labofina, S.A., Brussels, Belgium

[21] Appl. No.: 719,198

[22] Filed: Apr. 3, 1985

[30] Foreign Application Priority Data

Apr. 3, 1984 [LU] Luxembourg ............................ 85285

[51] Int. Cl.[4] .................................................. C07C 5/27
[52] U.S. Cl. ..................................... 585/671; 585/664; 585/666; 585/415
[58] Field of Search ................. 585/671, 664, 666, 415

[56] References Cited

U.S. PATENT DOCUMENTS

| | | | |
|---|---|---|---|
| 4,150,062 | 4/1979 | Garwood et al. | 585/415 |
| 4,309,275 | 1/1982 | Mulaskey | 585/654 |
| 4,387,260 | 6/1983 | Watson et al. | 585/467 |

FOREIGN PATENT DOCUMENTS 2114999  9/1983  United Kingdom ............... 585/467

Primary Examiner—John Doll
Assistant Examiner—A. Pal
Attorney, Agent, or Firm—John K. Abokhair; M. Norwood Cheairs

[57] ABSTRACT

A process for the isomerization of n-butenes, comprising contacting, at elevated temperatures, a feed containing n-butenes with a catalyst comprising a crystalline silica polymorph of the silicalite type in the presence of stream to recover a steam containing isobutene. The reaction can be carried out in either liquid or vapor phase.

10 Claims, No Drawings

PROCESS FOR THE ISOMERIZATION OF OLEFINS

FIELD OF THE INVENTION

The present invention relates to a process for the isomerization of olefins. More particularly, it relates to a process for the isomerization of n-butenes into isobutene.

BACKGROUND OF THE INVENTION

The environmental and other governmental measures adopted by several countries against the use of tetraethyllead in motor-fuel led the petroleum industry to seek other additives, including oxygen-containing additives, for improving the octane number of motor-fuel. Among these additives, asymmetric ethers, and more particularly methyl tert-butyl ether (MTBE), have proved to be very efficient gasoline additives. The most common method for the preparation of MTBE comprises the reaction of isobutene with methanol.

Isobutene is also used as starting material for the production of other valuable compounds, such as t-butyl alcohol (used as solvent), t-butyl phenol (used as stabilizer), low molecular weight polymers (used to improve the viscosity index of lubricating oils), etc. As a result of this increased interest in isobutenes, the present availability of isobutene does not allow the production of sufficient amounts of these derivatives to satisfy their potential market.

Accordingly, it can be seen that presently there is a need for a process to simply and economically produce isobutene, and particularly, a process that can utilize starting materials which are readily available.

SUMMARY OF THE INVENTION

An object of the present invention is to provide a new process for the production of isobutene.

Another object of the present invention is to provide a new process which enables to economically isomerize n-butenes into isobutene.

A further object of the present invention is to provide a process which enables to selectively produce isobutene from n-butenes or from a feedstock containing n-butenes.

The process of the present invention comprises contacting a n-butene-containing feedstock with a catalyst consisting of a crystalline silica polymorph of the silicalite type, in the presence of steam, the molar ratio water/feed being from about 0.5 to about 5.

DETAILED DESCRIPTION OF THE PREFERRED EMBODIMENTS

As starting feedstock for the process of the invention, substantially pure 1-butene or 2-butene or mixtures of both these isomers or still fractions which contain these isomers in admixture with other hydrocarbons may be used. The process of the invention may be applied to feeds having n-butenes content as low as 10% by volume.

The catalyst utilized in the present invention is an unmodified crystalline silica polymorph of the silicalite type. Therefore, the catalyst is a substantially pure silica, which means that said silica does not contain any impurities or any modifying elements, except traces thereof. A method for preparing silicalite together with the structure of silicalite are disclosed in U.S. Pat. No. 4,061,724 of Grose, which is hereby incorporated by reference in its entirety.

The n-butenes-containing feedstock is contacted with silicalite in the presence of steam. It is known that silicalite may be used as catalyst for the oligomerization of olefins, as disclosed in U.S. Pat. Nos. 4,414,423, 4,417,086 and 4,417,088 of S. J. Miller, incorporated herein by reference. However, it has unexpectedly been found that the presence of water not only results in improving the life time of the catalyst, but also, and more particularly, favors the production of isobutene while reducing the formation of heavier products. Due to the presence of steam, the isobutene selectivity is increased by about 50%, the other operating conditions remaining the same. The term "isobutene selectivity" means the weight of formed isobutene per 100 parts by weight of converted feed. This improvement in selectivity is achieved even when the treatment of the feed is carried out in the presence of an amount of water of as little as about 0.5 mole of water per mole of feed. Comparative experiments have also shown that it is preferable to maintain a water/feed molar ratio which does not exceed about 5. This higher limit varies with several factors including the composition of the feed. The water/feed molar ratio is preferably lower than about 1.5 when the treated feed has a n-butenes content of about 10% by volume. Generally, the amount of water to be used is such that the water/feed molar ratio is from about 0.5 to about 3; said ratio may however be higher if the feed has a high n-butenes content.

The process of the invention is very flexible and may be carried out in the gaseous phase and/or in the liquid phase.

The reaction temperature is generally from about 300 to about 550° C. Temperatures lower than 300° C. give very low yields, while temperatures higher than 550° C. lead to a degradation of the reaction products.

Preferably, the temperature is from about 300 to about 500° C., and more preferably, from about 320° to about 475° C.

Temperature variations between these limits do not significantly modify the distribution of the formed products.

The hourly space velocity of the reaction mixture, expressed by the weight of said mixture treated by weight of catalyst in one hour (WHSV), may vary between about 5 and 150 inclusive. The WHSV typically depends on the composition of the feed. On the other hand, a high hourly space velocity enables one to improve the selectivity of the process for the formation of isobutene. When a feedstock which essentially consists of n-butene is used, the WHSV is selected between about 5 and 100 inclusive, while with a feedstock which contains about 10% of n-butenes, the WHSV is selected between about 5 and 20 inclusive.

The reaction is generally carried out at an absolute pressure which may vary between wide limits, generally between sub-atmospheric pressures and 50 bars.

Typical absolute pressures are between 0.5 and 20 bars inclusive.

It is advantageous to operate at not very elevated pressures to favor the production of isobutene.

One skilled in the art can easily determine the operating conditions, among the ranges hereabove defined, which lead to the best yields in function not only of the composition of the treated feedstock, but also of the desired results. Certain conditions, particularly a high WHSV, favor the formation of isobutene with a low conversion rate of the feed. In these conditions, it is advantageous to recover the isobutene from the reaction products and to recycle these latter for additional treatment in the presence of fresh feed.

The following examples are meant to illustrate the process of the present invention but without limiting it.

EXAMPLE 1

1-butene was passed together with steam on silicalite at a temperature of 302° C. and under an absolute pressure of 1 bar, with a water/feed molar ratio of 3.42 and a WHSV of 6.22.

85.6% of 1-butene were converted and the isobutene selectivity was 13.33%.

By way of comparison, a similar experiment was carried out but in the absence of water. The isobutene selectivity was only 7.79%.

EXAMPLE 2

The procedure of Example 1 was repeated, but with a water/feed molar ratio of 1.66.

85.8% of 1-butene were converted and the isobutene selectivity was 12.95%.

EXAMPLE 3

A feed containing 60% by weight of isobutane and 40% by weight of n-butenes, was passed together with steam on silicalite at a temperature of 319° C., at a gauge pressure of 2 bar, a WHSV of 5.3 and a water/feed molar ratio of 0.88. 86.6% of butenes were converted and the isobutene selectivity was 15.61%.

EXAMPLE 4

A feed containing 49% by weight of n-butenes, 49.6% by weight of n-butane and 1.4% by weight of light hydrocarbons, was passed together with steam on silicalite at a temperature of 425° C., an absolute pressure of 1.6 bar, a WHSV of 31.1 and a water/feed molar ratio of 1.16.

72.8% of butenes were converted and the isobutene selectivity was 14.03%.

EXAMPLE 5

A feed containing 49% by weight of n-butenes, 49.6% by weight of n-butane and 1.4% by weight of light hydrocarbons was passed together with steam, on silicalite at a temperature of 325° C., an absolute pressure of 1.6 bar, a WHSV of 31.4 and a water/feed molar ratio of 1.11.

79.4% of butenes were converted and the isobutene selectivity was 12.5%.

This example shows that in the considered range of temperatures from 300° to 500° C., a temperature variation has practically no influence on the distribution of the formed products.

By way of comparison, the same feed was passed but in the absence of steam, while maintaining the other operating conditions:

| | |
|---|---|
| temperature: | 322° C. |
| absolute pressure | 14.8 bar |
| WHSV: | 33.2 |

89% of butenes were converted but the isobutene selectivity was only 5.99%.

As can be seen from the above, the process of the present invention results in the production of substantially above stoichiometric amounts of isobutene.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What we claim is:

1. A process for the isomerization of n-butenes wherein said process comprises the steps of:
   (a) contacting at a temperature of about 300° C. or higher, a feed containing at least 10% by volume n-butenes with a catalyst consisting essentially of a crystalline silica polymorph silicalite in the presence of a sufficient amount of steam such that the water/feed molar ratio is from about 0.5 to about 5; and
   (b) recovering a stream containing isobutene.

2. The process of claim 1, wherein the water/feed molar ratio is from about 0.5 to about 3.

3. The process of claim 1, wherein step (a) is carried out at a temperature of from about 300° C. to about 550° C.

4. The process of claim 1, wherein step (a) is carried out at a temperature of from about 320° C. to about 475° C.

5. The process of claim 1, wherein step (a) is carried out at a weight of reaction mixture per hour and weight of catalyst (WHSV) of from about 5 to about 150.

6. The process of claim 1, wherein step (a) is carried out at a weight of reaction mixture per hour and weight of catalyst (WHSV) of from about 5 to about 100.

7. The process of claim 1 wherein step (a) is carried out at an absolute pressure of from about sub-atmospheric to about 50 bars.

8. The process of claim 1 wherein step (a) is carried out at an absolute pressure of from about 0.5 to about 20 bars.

9. A process for the isomerization of n-butenes wherein said process comprises the steps of:
   (a) contacting, at a temperature of from about 320° C. to about 475° C. and under an absolute pressure of from about 0.5 bars to about 20 bars, a feed containing at least 10% by volume n-butenes with a catalyst consisting essentially of a crystalline silica polymorph silicalite in the presence of a sufficient amount of steam such that the water/feed molar ratio is from about 0.5 to about 1.5; and
   (b) recovering a stream containing isobutene.

10. A process for the isomerization of n-butenes wherein said process comprises the steps of:
    (a) contacting, at a temperature of from about 300° C. to about 550° C. and under an absolute pressure of from about 0.5 bars to about 50 bars, a feed containing at least 10% by volume n-butenes with a catalyst consisting essentially of a crystalline silica polymorph silicalite in the presence of a sufficient amount of steam such that the water/feed molar ratio is from about 0.5 to about 5; and
    (b) recovering a stream containing isobutene.

* * * * *